United States Patent [19]
DeLuca et al.

[11] Patent Number: 5,880,113
[45] Date of Patent: *Mar. 9, 1999

[54] 19-NOR-VITAMIN D COMPOUNDS

[75] Inventors: Hector F. DeLuca, Deerfield; Heinrich K. Schnoes; Kato L. Perlman, both of Madison, all of Wis.; Rafal R. Sicinski, Warsaw, Poland; Jean Martin Prahl, Madison, Wis.

[73] Assignee: Wisconsin Alumni Research Foundation, Madison, Wis.

[ * ] Notice: The term of this patent shall not extend beyond the expiration date of Pat. Nos. 5,185,150, 5,587,497, 5,321,018, and 5,086,191.

[21] Appl. No.: 626,431

[22] Filed: Apr. 25, 1996

Related U.S. Application Data

[62] Division of Ser. No. 442,492, May 16, 1995, Pat. No. 5,587,497, which is a division of Ser. No. 281,261, Jul. 27, 1994, abandoned, which is a division of Ser. No. 123,485, Sep. 17, 1993, Pat. No. 5,342,975, which is a division of Ser. No. 960,241, Oct. 13, 1992, Pat. No. 5,246,925, which is a continuation of Ser. No. 879,706, May 5, 1992, abandoned, which is a continuation of Ser. No. 557,400, Jul. 23, 1990, abandoned, which is a division of Ser. No. 481,354, Feb. 16, 1990, Pat. No. 5,237,110, which is a continuation-in-part of Ser. No. 321,030, Mar. 9, 1989, abandoned.

[51] Int. Cl.$^6$ .......................... A01N 45/00; C07C 401/00
[52] U.S. Cl. ............................................. 514/167; 552/653
[58] Field of Search .............................. 552/653; 514/167

[56] References Cited

U.S. PATENT DOCUMENTS 5,587,497  12/1996  DeLuca et al. .......................... 552/653

*Primary Examiner*—José G. Dees
*Assistant Examiner*—Alton N. Pryor
*Attorney, Agent, or Firm*—Andrus, Sceales, Starke & Sawall

[57] ABSTRACT

This invention provides a novel class of vitamin D-related compounds, namely the 1c-hydroxy-19-nor-vitamin D analogs, as well as a general method for their chemical synthesis. The compounds exhibit pronounced activity in arresting the proliferation of undifferentiated cells, including malignant cells, and in inducing their differentiation, and thus represent novel therapeutic agents for the treatment of malignant and other diseases characterized by the proliferative growth of undifferentiated cells. Formulations for therapeutic use and treatment methods are also provided.

7 Claims, No Drawings

19-NOR-VITAMIN D COMPOUNDS

This application is a divisional of application Ser. No. 08/442,492 filed May 16, 1995, now U.S. Pat. No. 5,587, 497, which in turn is a divisional of Ser. No. 08/281,261 filed Jul. 27, 1994, abn which in turn is a divisional of Ser. No. 08/123,485 filed Sep. 17, 1993, now U.S. Pat. No. 5,342, 975, which in turn is a divisional of Ser. No. 07/960,241 filed Oct. 13, 1992, now U.S. Pat. No. 5,246,925, which in turn is a continuation of Ser. No. 07/879,706 filed May 5, 1992, now abandoned, which in turn is a continuation of Ser. No. 07/557,400 filed Jul. 23, 1990 now abandoned, which in turn is a divisional of Ser. No. 07/481,354 filed Feb. 16, 1990, now U.S. Pat. No. 5,237,110, which in turn is a continuation in part application of Ser. No. 07/321,030 filed Mar. 9, 1989, now abandoned.

This invention was made with United States Government support awarded by the National Institutes of Health (NIH), Grant Number DK-14881. The United States Government has certain rights in this invention.

This invention relates to biologically active vitamin D compounds. More specifically, the invention relates to 19-nor-analogs of 1α-hydroxylated vitamin D compounds and to a general process for their preparation.

BACKGROUND

The 1α-hydroxylated metabolites of vitamin D—most importantly 1α, 25-dihydroxyvitamin $D_3$ and 1α,25-dihydroxyvitamin $D_2$—are known as highly potent regulators of calcium homeostasis in animals and humans, and more recently their activity in cellular differentiation has also been established. As a consequence, many structural analogs of these metabolites, such as compounds with different side chain structures, different hydroxylation patterns, or different stereochemistry, have been prepared and tested. Important examples of such analogs are 1α-hydroxyvitamin $D_3$, 1α-hydroxyvitamin $D_2$, various side chain fluorinated derivatives of 1α, 25-dihydroxyvitamin $D_3$, and side chain homologated analogs. Several of these known compounds exhibit highly potent activity in vito or in vitro, and possess advantageous activity profiles and thus are in use, or have been proposed for use, in the treatment of a variety of diseases such as renal osteodystrophy, vitamin D-resistant rickets, osteoporosis, psoriasis, and certain malignancies.

DISCLOSURE AND DESCRIPTION OF THE INVENTION

A class of 1α-hydroxylated vitamin D compounds not known heretofore are the 19-nor-analogs, i.e. compounds in which the ring A exocyclic methylene group (carbon 19) typical of all vitamin D system has been removed and replaced by two hydrogen atoms. Structurally these novel analogs are characterized by the general formula I shown below:

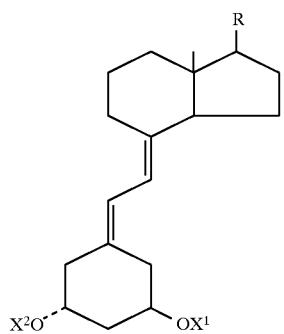

where $X^1$ and $X^2$ are each selected from the group consisting of hydrogen and acyl, and where the group R represents any of the typical side chains known for vitamin D type compounds. Thus, R may be an alkyl, hydrogen, hydroxyalkyl or fluoroalkyl group, or R may represent the following side chain:

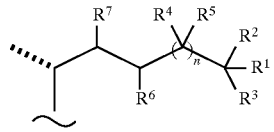

wherein $R^1$ represents hydrogen, hydroxy or O-acyl, $R^2$ and $R^3$ are each selected from the group consisting of alkyl, hydroxyalkyl and fluoroalkyl, or, when taken together represent the group—$(CH_2)_m$—where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, fluorine, alkyl, hydroxyalkyl and fluoroalkyl, or, $R^4$ and $R^5$ taken together represent double-bonded oxygen, $R^6$ and $R^7$ are each selected from the group consisting of hydrogen, hydroxy, O-acyl, fluorine and alkyl, or, $R^6$ and $R^7$ taken together form a carbon-carbon double bond, and wherein n is an integer having a value of from 1 to 5, and wherein the carbon at any one of positions 20, 22, or 23 in the side chain may be replaced by an O, S, or N atom.

Specific important examples of side chains are the structures represented by formulas (a), (b), (c), (d) and (e) below, i.e. the side chain as it occurs in 25-hydroxyvitamin $D_3$ (a); vitamin $D_3$ (b); 25-hydroxyvitamin $D_2$ (c); vitamin $D_2$ (d); and the C-24-epimer of 25-hydroxyvitamin $D_2$ (e).

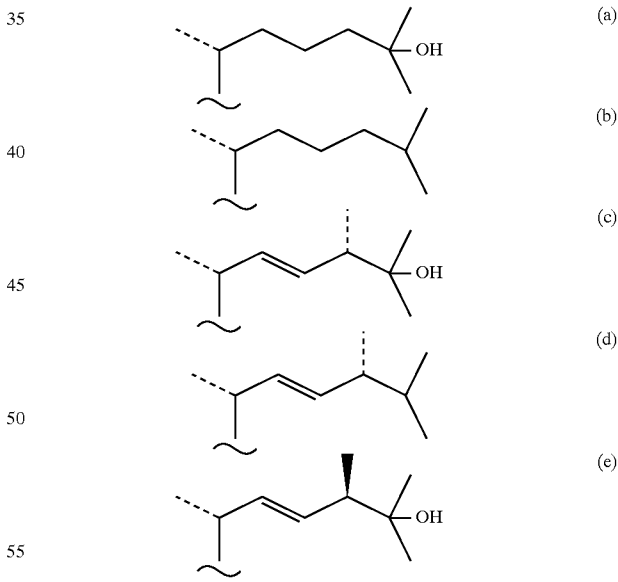

In this specification and the claims, the 'alkyl' signifies an alkyl radical of 1 to 5 carbons in all isomeric forms, such as methyl, ethyl, propyl, isopropyl, butyl, isobutyl, pentyl, etc., and the terms 'hydroxyalkyl' and 'fluoroalkyl' refer to such an alkyl radical substituted by one or more hydroxy or fluoro groups respectively, and the term 'acyl' means an aliphatic acyl group of 1 to 5 carbons, such as formyl, acetyl, propionyl, etc. or an aromatic acyl group such as benzoyl, nitrobenzoyl or halobenzoyl. The term 'aryl' signifies a phenyl-, or an alkyl-, nitro- or halo-substituted phenyl group.

The preparation of 1α-hydroxy-19-nor-vitamin D compounds having the basic structure shown above can be accomplished by a common general method, using known vitamin D compounds as starting materials. Suitable starting materials are, for example, the vitamin D compounds of the general structure II:

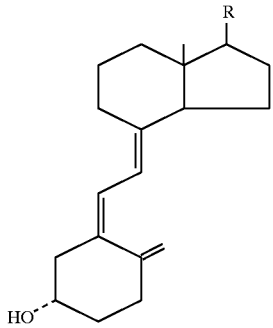

II where R is any of the side chains as defined above. These vitamin D starting materials are known compounds, or compounds that can be prepared by known methods.

Using the procedure of DeLuca et al. (U.S. Pat. No. 4,195,027), the starting material is converted to the corresponding 1α-hydroxy-3,5-cyclovitamin D derivative, having the general structure III below, where X represents hydrogen and Q represents an alkyl, preferably methyl:

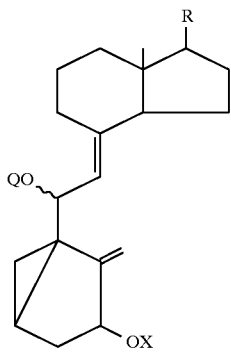

III

So as to preclude undesired reaction of the 1α-hydroxy group in subsequent steps, the hydroxy group is converted to the corresponding acyl derivative, i.e. the compound III shown above, where X represents an acyl group, using standard acylation procedures, such as treatment with an acyl anhydride or acyl halide in pyridine at room temperature or slightly elevated temperature (30°–70° C.). It should be understood also that whereas the process of this invention is illustrated here with acyl protection of hydroxy functions, alternative standard hydroxy-protecting groups can also be used, such as, for example, alkylsilyl or alkoxyalkyl groups. Such protecting groups are well-known in the art (e.g. trimethylsilyl, triethylsilyl, t.-butyldimenthylsilyl, or tetrahydrofuranyl, methoxymethyl), and their use is considered a routine modification of experimental detail within the scope of the process of this invention.

The derivative as obtained above is then reacted with osmium tetroxide, to produce the 10,19-dihydroxy analog, IV (where X is acyl), which is subjected to diol cleavage using sodium metaperiodate or similar vicinal diol cleavage reagents (e.g. lead tetraacetate) to obtain the 10-oxo-intermediate, having the structure V below (where X is acyl):

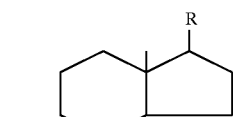

IV

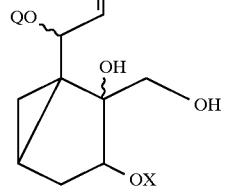

V

These two consecutive steps can be carried out according to the procedures given by Paaren et al. [J. Org. Chem. 48, 3819 (1983)]. If the side chain unit, R, carries vicinal diols (e.g. 24, 25-dihydroxy- or 25, 26-dihydroxy, etc.), these, of course, also need to be protected, e.g. via acylation, silylation, or as the isopropylidene derivative prior to the periodate cleavage reactions.

In most cases, the acylation of the 1α-hydroxy group as mentioned above will simultaneously effect the acylation of side chain hydroxy functions, and these acylation conditions can, of course, by appropiately adjusted (e.g. elevated temperatures, longer reaction times) so as to assure complete protection of side chain vicinal diol groupings.

The next step of the process comprises the reduction of the 10-oxo-group to the corresponding 10-alcohol having the structure VI shown below (where X is acyl and Y represents hydroxy). When X is acyl, this reduction is carried out conveniently in an organic solvent at from about 0° C. to about room temperature, using $NaBH_4$ or equivalent hydride reducing agents, selective for the reduction of carbonyl groups without cleaving ester functions. Obviously, when X is a hydroxy-protecting group that is stable to reducing agents, any of the other hydride reducing agents (e.g. $LiAlH_4$, or analogous reagents) may be employed also.

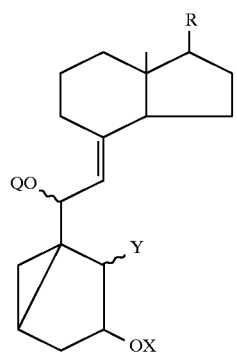

VI

The 10-hydroxy intermediate is then treated with an alkyl- or arylsulfonylhalide (e.g. mathanesulfonylchloride) in a suitable solvent (e.g. pyridine) to obtain the correpsonding 10-0-alkyl- or arylsulfonyl derivative (the compound having the structure shown VI above, where Y is alkyl-$SO_2O—$, or aryl-$SO_2O—$, and this sulfonate intermediate is then directly reduced, with lithiun aluminum hydride, or the analogous known lithium aluminum alkyl hydride reagents in an ether solvent, at a temperature ranging from 0° C. to the boiling temperature of the solvent, thereby displacing the sulfonate group and obtaining the 10-deoxy derivative, represented by the structure VI above, where X and Y are both hydrogen. As shown by the above structure, a 1-0-acyl function in the precursor compound V is also cleaved in this reduction step to produce the free 1c-hydroxy function, and any 0-acyl protecting group in the side chain would, of course, likewise be reduced to the corresponding free alcohol function, as is well understood in the art. If desired, the hydroxy groups at C-1 (or hydroxy groups in the side chain) can be reprotected by acylation or silylation or ether formation to the corresponding acyl, alkylsilyl or alkoxyalkyl derivative, but such protection is not required. Alternative hydroxy-protecting groups, such as alkylsilyl or alkoxyalkyl groups would be retained in this reduction step, but can be removed, as desired, at this or later stages in the process by standard methods known in the art.

The above 1c-hydroxy-10-deoxy cyclovitamin D intermediate is next solovolyzed in the presence of a low-molecular weight organic acid, using the conditions of DeLuca et al. (U.S. Pat. Nos. 4,195,027 and 4,260,549). When the solvolysis is carried out in acetic acid, for example, there is obtained a mixture of 1α-hydroxy-19-nor-vitamin D 3-acetate and 1α-hydroxy-19-nor-vitamin D 1-acetate (compounds VII and VIII, below), and the analogous 1- and 3-acylates are produced, when alternative acids are used for solvolysis.

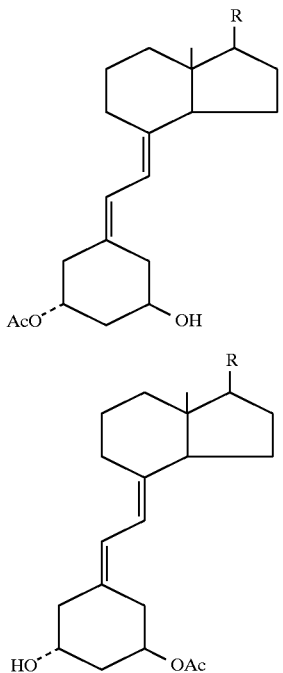

Direct basic hydrolysis of this mixture under standard conditions then produces the desired 1α-hydroxy-19-nor-vitamin D compounds of structure I above (where $X^1$ and $X^2$ are hydrogen). Alternatively, the above mixture of monacetates may also be separated (e.g. by high pressure liquid chromatography) and the resulting 1-acetate and 3-acetate isomers may be subjected separately to hydrolysis to obtain the same final product from each, namely the 1α-hydroxy-19nor-vitamin D compounds of structure I. Also the separated monoacetates of structure VII or VIII or the free 1,3-dihydroxy compound can, of course, be reacylated according to standard procedures with any desired acyl group, so as to produce the product of structure I above, where $X^1$ and $X^2$ represent acyl groups which may be the same or different.

Biological Activity of 1α-Hydroxy-19-Nor-Vitamin D Compounds

The novel compounds of this invention exhibit an unexpected pattern of biological activity, namely high potency in promoting the differentiation of malignant cells and little or no activity in calcifying bone tissue. This is illustrated by the biological assay results obtained for α, 25-dihydroxy-19-nor-vitamin $D_3$ (compounds Ia), which are summarized in Tables 1 and 2, respectively. Table 1 shows a comparison of the activity of the known active metabolite 1α, 25-dihydroxyvitamin $D_3$ and the 19-nor analog (Ia) in inducing the differentiation of human leukemia cells (HL-60 cells) in culture to normal cells (monocytes). Differentiation activity was assessed by three standard differentiation assays, abbreviated in Table 1 as NBT (nitroblue tetrazolium reduction), NSE (non-specific esterase activity), and PHAGO (phagocytosis activity). The assays were conducted according to known procedures, as given, for example, by DeLuca et al. (U.S. Pat. No. 4,717,721) and Ostrem et al., J. Biol. Chem. 262, 14164, 1987). For each assay, the differentiation activity of the test compounds is expressed in terms of the percent of HL-60 cells having differentiated to normal cells in response to a given concentration of test compound.

The results summarized in Table 1 clearly show that the new analog, 1α-dihydroxy-19-nor-vitamin $D_3$ (Ia) is a potent as α, 25-dihydroxyvitamin $D_3$ in promoting the differentiation of leukemia cells. Thus in all three assays close to 90% of the cells are induced to differentiate by 1c, 25-dihdyroxy-vitamin $D_3$ at a concentration of $1\times10^{-7}$ molar, and the same degree of differentiation (i.e. 90, 84, and 90%) is achieved by the 19-nor analog (Ia).

TABLE 1

| Differentiation of HL-60 Cells | | | |
|---|---|---|---|
| | % Differentiated Cells (mean ± SEM) | | |
| | NBT | NSE | PHAGO |
| 1α, 25-dihydroxyvitamin $D_3$ (moles/liter) | | | |
| $1 \times 10^{-7}$ | 86 ± 2 | 89 ± 1 | 87 ± 3 |
| $1 \times 10^{-8}$ | 60 ± 2 | 60 ± 3 | 64 ± 2 |
| $1 \times 10^{-9}$ | 33 ± 2 | 31 ± 2 | 34 ± 1 |
| 1α, 25-Dihydroxy-19-nor-vitamin $D_3$, (Ia) (moles/liter) | | | |
| $2 \times 10^{-7}$ | 94 ± 2 | 95 ± 3 | 94 ± 2 |
| $1 \times 10^{-7}$ | 90 ± 4 | 84 ± 4 | 90 ± 4 |
| $5 \times 10^{-8}$ | 72 ± 3 | 73 ± 3 | 74 ± 3 |
| $1 \times 10^{-8}$ | 61 ± 3 | 60 ± 3 | 56 ± 1 |
| $1 \times 10^{-9}$ | 32 ± 1 | 31 ± 1 | 33 ± 1 |

In contrast to the preceding results, the new 19-nor analog (Ia) exhibits no activity in an assay measuring the calcification of bone, a typical response elicited by vitamin D compounds. Relevant data, representing the results of an assay comparing the bone calcification activity in rats of 1α, 25-dihydroxyvitamin $D_3$ and 1α, 25-dihydroxy-19-nor-vitamin $D_3$ (Ia), are summarized in Table 2. This assay was conducted according to the procedure described by Tanaka et al., Endocrinology 92, 417 (1973).

The results presented in Table 2 show the expected bone calcification activity of α, 25-dihydroxyvitamin $D_3$ as reflected by the increase in percent bone ash, and in total ash at all dose levels. In contrast, the 19-nor analog Ia exhibits no activity at all three dose levels, when compared to the vitamin D-deficient (-D) control group.

TABLE 2

Calcification Activity

| Compound | Amount Administered* (pmoles/day/ 7 days) | % Ash (mean ± SEM) | Total Ash (mg) (mean ± SEM) |
|---|---|---|---|
| -D (control) | 0 | 19 ± 0.8 | 23 ± 1.2 |
| 1α, 25-dihydroxy-vitamin $D_3$ | 32.5 | 23 ± 0.5 | 34 ± 1.6 |
| | 65.0 | 26 ± 0.7 | 36 ± 1.1 |
| | 325.0 | 28 ± 0.9 | 40 ± 1.9 |
| 1α, 25-dihydoroxy-19-nor-vitamin $D_3$ (Ia) | 32.5 | 22 ± 0.9 | 28 ± 1.6 |
| | 65.0 | 19 ± 0.9 | 28 ± 3.4 |
| | 325.0 | 19 ± 1.2 | 30 ± 2.4 |

*Each assay group comprised 6 rats, receiving the indicated amount of test compound by intraperitoneal injection daily for a period of seven days.

Thus the new 19-nor analog shows a selective activity profile combining high potency in inducing the differentiation of malignant cells with very low or no bone calcification activity. The compounds of this novel structural class, therefore, can be useful as therapeutic agents for the treatment of malignancies. Because the differentiative activity of vitamin D compounds on keratinocytes of skin (Smith et al., J. Invest. Dermatol. 86, 709, 1986; Smith et al., J. Am. Acad. Dermatol. 19, 516, 1988) is believed to be an indication of successful treatment of psoriasis (Takamoto et al., Calc. Tissue Int. 39, 360, 1986), these compounds should prove useful in treating this and other skin disorders characterized by proliferation of undifferentiated skin cells. These compounds should also find use in the suppression of parathyroid tissue, as for example, in cases of secondary hyperparathyroidism found in renal disease (Slatopolsky et al., J. Clin. Invest. 74, 2136, 1984).

For treatment purposes, the novel compounds of this invention can be formulated as solutions in innocuous solvents, or as emulsions, suspensions or dispersions in suitable innocuous solvents or carriers, or as pills, tablets or capsules, containing solid carriers according to conventional methods known in the art. For topical applications the compounds are advantageously formulated as creams or ointments or similar vehicle suitable for topical applications. Any such formulations may also contain other pharmaceutically-acceptable and non-toxic excipients such as stabilizers, anti-oxidants, binders, coloring agents or emulsifying or taste-modifying agents.

The compounds are advantageously administered by injection, or by intravenous infusion of suitable sterile solutions, or in the form of oral doses via the alimentary canal, or topically in the form of ointments, lotions, or in suitable transdermal patches. For the treatment of malignant diseases, the 19-nor-vitamin D compounds of this invention are administered to subjects in dosages sufficient to inhibit the proliferation of malignant cells and induce their differentiation into normal monocyte-macrophages. Similarly, for the treatment of psoriasis, the compounds may be administered orally or topically in amounts sufficient to arrest the proliferation of undifferentiated keratinocytes, and in the treatment of hyperparathyroidism, the compounds are administered in dosages sufficient to suppress parathyroid activity, so as to achieve parathyroid hormone levels in the normal range. Suitable dosage amounts are from 1 to 500 μg of compound per day, such dosages being adjusted, depending on diseases to be treated, its severity and the response or condition of the subject as well-understood in the art.

This invention is more specifically described by the following illustrative examples. In these examples specific products identified by Roman numerals and letters, i.e. Ia, Ib, . . . , IIa, IIb, . . . , etc. refer to the specific structures and side chain combinations identified in the preceding description.

EXAMPLE 1

Preparation of 1α, 25-dihydroxy-19-nor-vitamin $D_3$ (Ia)

(a) 1α, 25-Dihydroxy-3, 5-cyclovitamin $D_3$ 1acetate, 6methyl ether: Using 25-hydroxyvitamin $D_3$ (IIa) as starting material, the known 1c, 25-dihydroxy-3, 5-cyclovitamin $D_3$ derivative IIIa (X=H) was prepared according to published procedures (DeLuca et al., U.S. Pat. No. 4,195,027 and Paaren et al., J. Org. Chem. 45, 3252 (1980)). This product was then acetylated under standard conditions to obtain the corresponding 1-acetate derivative IIIa (X=Ac).

(b) 10, 19-Dihydro-1α, 10, 19, 25-tetrahydroxy-3, 5-cyclovitamin $D_3$ 1acetate, 6-methyl ether (IVa): Intermediate IIIa (X=Ac) was treated with a slight molar excess of osmium tetroxide in pyridine according to the general procedure described by Paaren et al. (J. Org. Chem. 48, 3819 (1983)) to obtain the 10, 19-dihydroxylated derivative IVa. Mass spectrum m/z (relative intensity), 506 ($M^+$, 1), 488 (2), 474 (40), 425 (45), 396 (15), 285 (5), 229 (30), 133 (45), 59 (80), 43 (100). $^1H$ NMR ($CDCl_3$) δ 0.52 (3H, s, 18-$CH_3$), 0.58 (1H, m 3-H), 0.93 (3H, d J=6.1 Hz, 21-$CH_3$), 1.22 (6H, s, 26-$CH_3$ and 27-$CH_3$), 2.10 (3H, s, $COCH_3$), 3.25 (3H, s 6-$OCH_3$), 3.63 (2H, m, 19-$CH_2$), 4.60 (1H, d, J=9.2 Hz, 6-H), 4.63 (1H, dd, 1β-H), 4.78 (1H, d, J=9.2 Hz, 7-H).

(c) 1α, 25-Dihydroxy-10-oxo-3, 5-cyclo-19-nor-vitamin $D_3$ 1-acetate, 6-methyl ether (Va): The 10, 19-dihydroxylated intermediate IVa was treated with a solution of sodium metaperiodate according to the procedure given by Paaren et al. (J. Org. Chem. 48, 3819, 1983) to produce the 10-oxo-cyclovitamin D derivative (Va, X=Ac). Mass spectrum m/z (relative intensity) 442 ($M^+$-MeOH) (18), 424 (8). 382 (15), 364 (35), 253 (55), 225 (25), 197 (53), 155 (85), 137 (100). $^1H$ NMR ($CDCl_3$) δ 0.58 (3H, s, 18-$CH_3$), 0.93 (3H, d, J=6.6 Hz, 21-$CH_3$), 1.22 (6H, s, 26-$CH_3$ and 27-$CH_3$), 2.15 (s, 3-$OCOCH_3$), 3.30 (3H, s, 6-$OCH_3$), 4.61 (1H, d, J=9.1 Hz, 6-H), 4.71 (1H, d, J=9.6 Hz, 7-H), 5.18 (1H, m, 1β-H).

It has been found also that this diol cleavage reaction does not require elevated temperatures, and it is, indeed, generally prefereable to conduct the reaction at approximately room temperature.

(d) 1c-Acetoxy-10, 25-dihydroxy-3, 5-cyclo-19-nor-vitamin $D_3$ 6-methyl ether (VIa, X=Ac, Y=OH): The 10-oxo derivative Va (X=Ac) (2.2 mg, 4.6 μmol) was dissolved in 0.5 ml of ethanol and to this solution 50 μl (5.3 μmol) of a $NaBH_4$ solution (prepared from 20 mg of $NaBH_4$, 4.5 ml water and 0.5 ml of 0.01 N NaOH solution) was added and the mixture stirred at 0° C. for ca. 1.5 h, and then kept at 0° C. for 16 h. To the mixture ether was added and the organic phase washed with brine, dried over $MgSO_4$, filtered and evaporated. The crude product was purified by column chromatography on a 15×1 cm silica gel column and the alcohol VIa (X=Ac, Y=OH) was eluted with ethyl acetate hexane mixtures to give 1.4 mg (3 μmol) of product. Mass spectrum m/z (relative intensity) 476 (M$^+$) (1), 444 (85), 426 (18), 384 (30), 366 (48), 351 (21), 255 (35), 237 (48), 199 (100), 139 (51), 59 (58).

(e) 1α, 25-Dihydroxy-19-nor-vitamin $D_3$ (Ia, $X^1=X^2=H$): The 10-alcohol (VIa, X=Ac, Y=OH) (1.4 mg) was dissolved in 100 μl anhydrous $CH_2Cl_2$ and 10 μl (14 μmol) triethylamine solution {prepared from 12 mg (16 μl) triethylamine in 100 μl anhydrous $CH_2Cl_2$}, followed by 7 μl (5.6 μmol) mesyl chloride solution (9 mg mesyl chloride, 6.1 μl, in 100 μl anhydrous $CH_2Cl_2$) added at 0° C. The mixture was stirred at 0° C. for 2 h. The solvents were removed with a stream of argon and the residue (comprising compound VIa, X=Ac, Y=$CH_3SO_2O$—) dissolved in 0.5 ml of anhydrous tetrahydrofuran; 5 mg of $LiAlH_4$ was added at 0° C. and the mixture kept at 0° C. for 16 h. Excess $LiAlH_4$ was decomposed with wet ether, the ether phase was washed with water and dried over $MgSO_4$, filtered and evaporated to give the 19-nor product VIa (X=Y=H).

This product was dissolved in 0.5 ml of acetic acid and stirred at 55° C. for 20 min. The mixture was cooled, ice water added and extracted with ether. The other phase was washed with cold 10% sodium bicarbonate solution, brine, dried over $MgSO_4$, filtered and evaporated to give the expected mixture of 3-acetoxy-1α-hydroxy- and 1α-acetoxy-3-hydroxy isomers, which were separated and purified by HPLC (Zorbax Sil column, 6.4×25 cm, 2-propanol in hexane) to give about 70 μg each of compounds VIIa and XIIIa. UV (in EtOH) $\lambda_{max}$ 242.5 (OD 0.72), 251.5 (OD 0.86), 260 (OD 0.57).

Both 19-nor-1, 25-dihydroxyvitamin $D_3$ acetates VIIa and VIIIa were hydrolyzed in the same manner. Each of the monoacetates was dissolved in 0.5 ml of ether and 0.5 ml 0.1 N KOH in methanol was added. The mixture was stirred under argon atmosphere for 2 h. More ether was added and the organic phase washed with brine, dried over anhydrous $MgSO_4$, filtered and evaporated. The residue was dissolved in a 1:1 mixture of 2-propanol and hexane and passed through a Sep Pak column and washed with the same solvent. The solvents were evaporated and the residue purified by HPLC (Zorbax Sil, 6.4×25 cm, 10% 2-propanol in hexane). The hydrolysis products of VIIa and VIIIa were identical and gave 66 μg of Ia ($X^1=X^2=H$). Mass spectrum (m/z relative intensity) 404 (M$^+$) (100), 386 (41), 371 (20), 275 (53), 245 (51), 180 (43), 135 (72), 133 (72), 95 (82), 59 (18), exact mass calcd. for $C_{26}H_{44}O_3$ 404.3290, found 404.3272. $^1$H NMR ($CDCl_3$) δ 0.52 (3H, s, 18-$CH_3$), 0.92 (3H, d, J=6.9 Hz, 21-$CH_3$), 1.21 (6H, s, 26-$CH_3$ and 27-$CH_3$), 4.02 (1H, m, 3α-H), 4.06 (1H, m, 1β-H), 5.83 (1H, d, J=11.6 Hz, 7-H), 6.29 (1H, d, J=10.7 Hz, 6-H). UV (in EtOH), $\lambda_{max}$ 243 (OD 0.725), 251.5 (OD 0.823), 261 (OD 0.598).

EXAMPLE 2

Preparation of 1α-hydroxy-19-nor-vitamin $D_3$ (Ib)

(a) With vitamin $D_3$ (IIb) as starting material, and utilizing the conditions of Example 1a, there is obtained known 1α-hydroxy-3, 5-cyclovitamin $D_3$ 1-acetate, 6-methyl ether, compound IIIb (X=Ac).

(b) By subjecting intermediate IIIb (X=Ac), as obtained in Example 2a above to the conditions of Example 1b, there is obtained 10, 19-dihydro-1α, 10, 19-trihydroxy-3, 5-cyclovitamin $D_3$ 1-acetate, 6-methyl ether IVb (X=Ac).

(c) By treatment of intermediate IVb (X=Ac) with sodium metaperiodate according to Example 1c above, there is obtained 1α-hydroxy-10-oxo-3, 5-cyclo-19-nor-vitamin $D_3$ 1-acetate, 6methyl ether Vb (X=Ac).

(d) Upon reduction of the 10oxo-intermediate Vb (X=Ac) under the conditions of Example 1d above, there is obtained 1α-acetoxy-10-hydroxy-3, 5cyclo-19-nor-vitamin $D_3$ 6-methyl ether VIb (X=Ac, Y=OH).

(e) Upon processing intermediate VIb (X=Ac), Y=OH) through the procedure given in Example 1e above, there is obtained 1α-hydroxy-19-nor-vitamin $D_3$ (Ib, $X^1=X^2=H$).

EXAMPLE 3

Preparation of α, 25-dihydroxy-19nor-vitamin $D_2$ (a) Utilizing 25-hydroxyvitamin $D_2$ (IIc) as starting material and experimental conditions analogous to those of Example 1a, there is obtained 1α, 25-dihydroxy-3, 5-cyclovitamin $D_2$ 1-acetate, 6-methyl ether, compound IIIc (X=Ac).

(b) Subjecting intermediate IIId (X=Ac), as obtained in Example 3a above, to the reaction conditions of Example Ib, provides 10, 19-dihydro-1c, 10, 19, 25-tetrahydroxy-3, 5-cyclo-vitamin $D_2$ 1-acetate, 6-methyl ether, IVc (X=Ac).

(c) By treatment of intermediate IVc (X=Ac) with sodium metaperiodate according to general procedures of Example 1c above, there is obtained 1α,25-dihydroxy-10-oxo-3, 5-cyclo-19-nor-vitamin $D_2$ 1-acetate, 6-methyl ether Vc (X=Ac).

(d) Upon reduction of the 10-oxo-intermediate Vc (X=Ac) under conditions analogous to those of Example 1d above, there is obtained 1αacetoxy-10, 25-dihydroxy-3, 5-cyclo-19-nor-vitamin $D_2$ 6methyl ether VIc (X=Ac, Y=OH).

(e) Upon processing intermediate VIc (X=Ac, Y=OH) through the procedural steps given in Example 1e above, there is obtained 1α, 25-dihydroxy-19-nor-vitamin $D_2$ (Ic, $X^1=X^2=H$).

EXAMPLE 4

Preparation of 1α-hydroxy-19-nor-vitamin $D_2$ (a) With vitamin $D_2$ (IId) as starting material, and utilizing the conditions of Example 1a, there is obtained known 1c-hydroxy-3, 5-cyclovitamin $D_2$ 1-acetate, 6methyl ether, compound IIId (X=Ac).

(b) By subjecting intermediate IIId (X=Ac), as obtained in Example 4a above to the conditions of Example 1b, there is obtained 10, 19-dihydro-1α, 10, 19-trihydroxy-3, 5-cyclovitamin $D_2$ 1acetate, 6-methyl ether, IVd (X=Ac).

(c) By treatment of intermediate IVb (X=Ac) with sodium metaperiodate according to Example 1c above, there is obtained 1c-hydroxy-10-oxo-3, 5-cyclo-19-nor-vitamin $D_2$ 1-acetate, 6-methyl ether, Vd (X=Ac).

(d) Upon reduction of the 10-oxo-intermediate Vd (X=Ac) under the conditions of Example 1d above, there is obtained 1α-acetoxy-10-hydroxy-3, 5-cyclo-19-nor-vitamin $D_2$ 6-methyl ether, VId (X=Ac, Y=OH).

(e) Upon processing intermediate VId (X=Ac, Y=OH) through the procedure given in Example 1e above, there is obtained 1α-hydroxy-19-nor-vitamin $D_2$ (Id, $X^1=X^2=H$).

We claim:
1. A compound having the formula

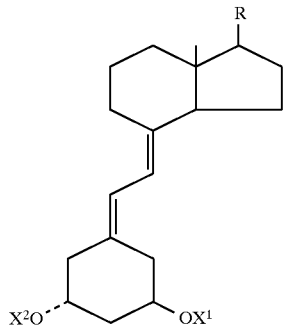

where $X^1$ and $X^2$ are each selected from hydrogen, acyl, alkylsilyl and alkoxyalkyl, and where R is selected from hydroxyalkyl, said hydroxyalkyl having from 2 to 3 carbon atoms.

2. A pharmaceutical composition comprising at least one compound having the formula

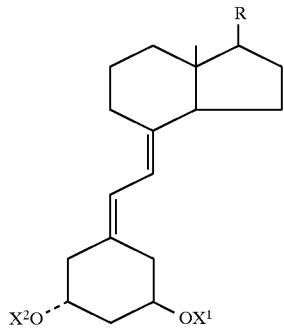

wherein $X^1$ and $X^2$ are each selected from hydrogen, acyl, alkylsilyl and alkoxyalkyl, and where R is selected from alkyl, hydrogen, hydroxyalkyl, fluoroalkyl and a side chain of the formula

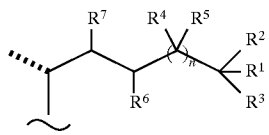

wherein $R^1$ represents hydrogen, hydroxy or O-acyl, $R^2$ and $R^3$ are each selected from alkyl, hydroxyalkyl and fluoroalkyl, or, when taken together represent the group—$(CH_2)_m$—where m is an integer having a value of from 2 to 5, $R^4$ is selected from hydrogen, hydroxy, fluorine, O-acyl, alkyl, hydroxyalkyl and fluoroalkyl, $R^5$ is selected from hydrogen, fluorine, alkyl, hydroxyalkyl and fluoroalkyl, or $R^4$ and $R^5$ taken together represent double-bonded oxygen, $R^6$ and $R^7$ are each selected from hydrogen, hydroxy, O-acyl, fluorine and alkyl, or, $R^6$ and $R^7$ taken together form a carbon-carbon double bond, and wherein n is an integer having a value of from 1 to 5 and wherein any of the groups—$CH(CH_3)$—, —$CH(R^7)$—, or $CH(R^6)$—at positions 20, 22 and 23, respectively, may be replaced by an oxygen atom, with the proviso that when n is 2 to 5 each $R^4$ is independently selected from hydrogen, hydroxy, fluorine, O-acyl, alkyl, hydroxyalkyl and fluoroalkyl, and each $R^5$ is independently selected from hydrogen, fluorine, alkyl, hydroxyalkyl and fluoroalkyl.

3. A pharmaceutical composition according to claim 2 wherein the compound is in a solid or liquid vehicle ingestible by and non-toxic to mammals.

4. A pharmaceutical composition in accordance with claim 2 where the compound is 1α, 25-dihydroxy-19-nor-vitamin $D_3$.

5. A pharmaceutical composition in accordance with claim 2 where the compound is 1α-hydroxy-19-nor-vitamin $D_3$.

6. A pharmaceutical composition in accordance with claim 2 where the compound is α, 25-dihydroxy-19-nor-vitamin $D_2$.

7. A pharmaceutical composition in accordance with claim 2 where the compound is 1α-hydroxy-19nor-vitamin $D_2$.

* * * * *

UNITED STATES PATENT AND TRADEMARK OFFICE
CERTIFICATE OF CORRECTION

PATENT NO. : 5,880,113
DATED : March 9, 1999
INVENTOR(S) : Hector F. DeLuca et al It is certified that error appears in the above-indentified patent and that said Letters Patent is hereby corrected as shown below:

Claim 4, line 31: Delete "1α, 25" and substitute therefor ---1α,25---

Claim 6, line 37: Delete "α, 25" and substitute therefor ---1α,25---

Claim 7, line 40: Delete "1α-hydroxy-19nor-vitamin" and substitute therefor ---1α-hydroxy-19-nor-vitamin---

Signed and Sealed this

Twenty-fourth Day of August, 1999

Attest:

Q. TODD DICKINSON

*Attesting Officer*     *Acting Commissioner of Patents and Trademarks*